United States Patent [19]
Gagnon et al.

[11] Patent Number: 5,764,355
[45] Date of Patent: Jun. 9, 1998

[54] SPECTROSCOPIC SAMPLE HOLDER

[76] Inventors: David R. Gagnon; Richard M. Pieper; James E. Aysta, all of P.O. Box 33427, St. Paul, Minn. 55133-3427

[21] Appl. No.: 587,316

[22] Filed: Jan. 12, 1996

[51] Int. Cl.$^6$ .................................................. G01N 21/01
[52] U.S. Cl. .................... 356/244; 422/104; 422/102; 250/339.07; 436/164
[58] Field of Search .................... 356/244, 440, 356/319, 326, 246; 250/339.07, 343, 576; 436/164, 172; 422/99, 102, 104, 57; 435/805

[56] References Cited

U.S. PATENT DOCUMENTS

| | | | |
|---|---|---|---|
| 3,953,566 | 4/1976 | Gore | 264/288 |
| 3,962,153 | 6/1976 | Gore | 260/2.5 R |
| 4,096,227 | 6/1978 | Gore | 264/210 R |
| 4,110,392 | 8/1978 | Yamazaki | 264/127 |
| 4,187,390 | 2/1980 | Gore | 174/102 |
| 4,194,041 | 3/1980 | Gore et al. | 428/315 |
| 4,405,560 | 9/1983 | Murata | 422/102 |
| 4,539,256 | 9/1985 | Shipman | 428/315.5 |
| 4,562,045 | 12/1985 | Murata | 422/102 |
| 4,618,475 | 10/1986 | Wang . | |
| 5,290,705 | 3/1994 | Davis | 436/164 |
| 5,344,701 | 9/1994 | Gagnon et al. | 428/304.4 |
| 5,453,252 | 9/1995 | Truett | 422/104 |
| 5,470,757 | 11/1995 | Gagnon et al. | 356/36 |
| 5,519,218 | 5/1996 | Chang | 356/244 |
| 5,544,218 | 8/1996 | Turner et al. | 378/208 |

FOREIGN PATENT DOCUMENTS

| | | |
|---|---|---|
| 0 478 596 B1 | of 0000 | European Pat. Off. . |
| 867 192 | 5/1961 | United Kingdom . |
| WO 93 00580 A | 1/1993 | WIPO . |

OTHER PUBLICATIONS

*Review of Scientific Instruments*, by C.K. Williamson and G.N. Coleman, vol. 65, No. 6, Jun. 1, 1994, pp. 2155-2156.

Afran and Newbury, *Spectroscopy*, 6(1), pp. 31-34 (1990).

Prasad et al., "Non-dispersive Solvent Extraction Using Microporous Membranes," *AIChE Symposium*, Series No. 261, vol. 84, 42-53 (1988).

Baker et al., "Membrane Separation System—A Research and Development Needs Assessment," *Final Report*, vol. 2, U.S. Dept. of Energy, Office of Program Analysis (Mar. 1990), pp. index, introduction, and 6-i to 6-31.

W. L. Truett et al., "A Method for Determining the IR Spectra of Liquids and Solids," *American Laboratory*, Nov. 1995, pp. 20R-20T.

M. Meurens et al., "New System of Sample Presentation for Bacteria Identification By FTIR Spectroscopy," Internal Publication for the Université Catholique de Louvain (May 1994).

M. Meurens et al., "Fast Drying Systems for NIR Analysis," *Journal of NIR News*, 3(5), (Sep.-Oct. 1992) pp. 12-13 (pre-publication copy).

P. Chandley, "The Application of the DESIR Technique to the Analysis of Beer," *J. Near Infrared Spectrosc*, 1, pp. 133-139 (1993).

*Primary Examiner*—Hoa Q. Pham
*Attorney, Agent, or Firm*—Gary L. Griswold; Walter N. Kirn; William J. Bond

[57] ABSTRACT

A device for holding a sample to be spectroscopically analyzed in which the sample is retained within a defined area. The device includes a receiving medium on which the sample is held. When this receiving medium is mounted in a frame (an optional feature), it extends across an aperture in the frame. In/on the receiving medium is a sample confining region that keeps any sample placed on the receiving medium from migrating outside a defined area. By keeping the sample within a defined area, quantitative measurements of the sample can be obtained.

27 Claims, 8 Drawing Sheets

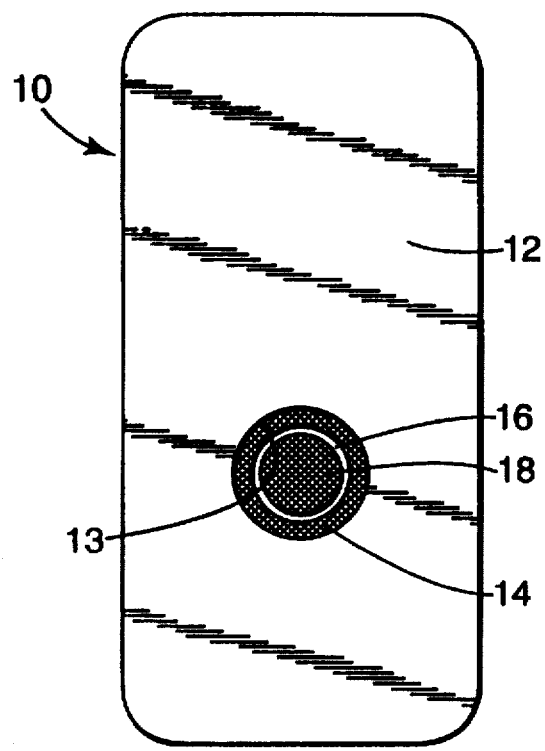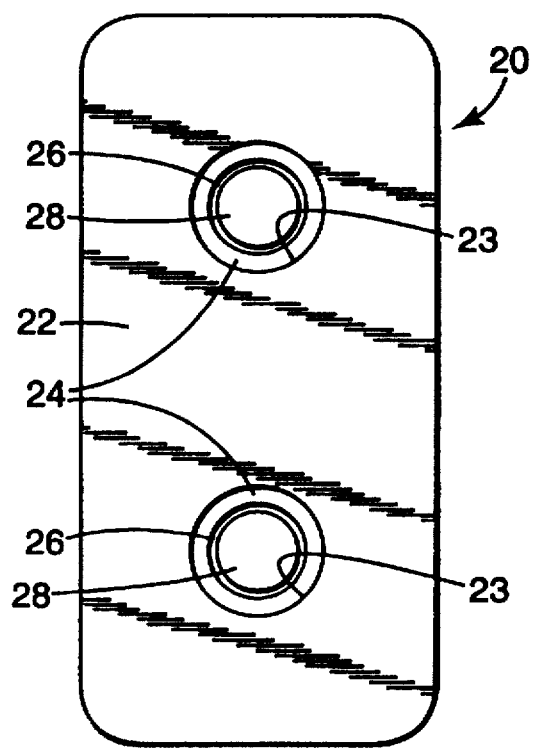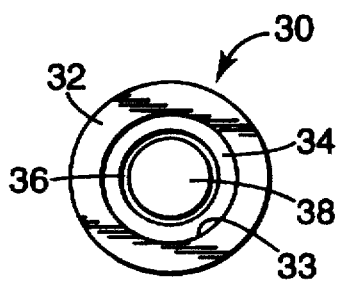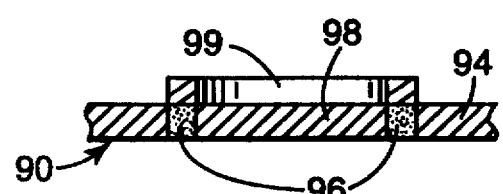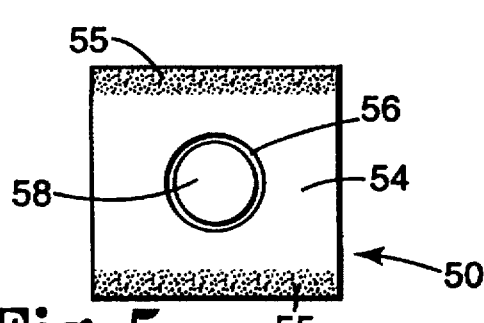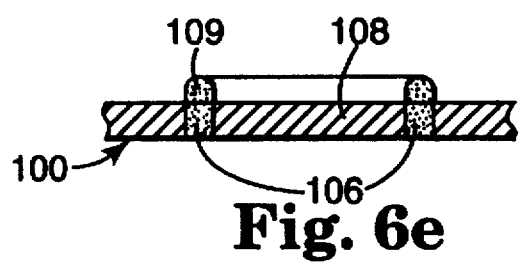

SPECTROSCOPIC SAMPLE HOLDER

BACKGROUND INFORMATION

1. Field of Invention

The present invention relates to a sample holder for use in spectroscopic analysis and method of using this sample holder.

2. Background of the Invention

Most chemical compounds absorb incident infrared (IR) radiation at frequencies corresponding to the vibrational frequencies of various chemical bonds in the compound. The structural features of a compound can be determined by passing a beam of IR light therethrough, comparing the transmitted light to that of the incident beam, and plotting the relative intensity of the sample beam as a function of wavelength or wavenumber so as to obtain a spectroscopic profile of the compound.

A sample holder or cell is used to hold a sample in the path of the incident IR light beam. The material used for the sample holder must be essentially transparent to IR radiation in the region of the IR spectrum of interest and should not be soluble in or reactive with the sample or any solvent that is used. Examples of materials commonly used in sample holders include inorganic salts, glasses, and quartz. Often, the holder (or cell) is constructed from a pair of plates made from precisely machined and polished crystals of an inorganic salt (e.g., NaCl).

Solid samples often are ground and intimately mixed with an inorganic salt (e.g., KBr), pressed into a thin wafer or pellet, and mounted onto a sample holder. Alternatively, they can be mulled with an oil (e.g., NUJOL™ mineral oil) and the resulting mixture applied to a previously described plate.

Liquid samples, either neat or in solvent, normally are analyzed in "cells". A cell is a pair of plates sealed together with a spacer to provide a chamber in which the sample is held. The plates are spaced a set distance apart, providing a sample chamber of a known volume and path length which can be used for quantitative measurements. Such cells must be thoroughly cleaned between uses, often with hazardous solvents. This limits their ability to be used in large scale, automated analytical testing configurations. Also, frequent handling can lead to increased breakage or deterioration, resulting in additional maintenance time and expense.

In addition to plates, other sample preparation techniques have been developed. The Background section of U.S. Pat. No. 5,470,757 describes several alternative sample preparation and holding methods that have been developed over the past several decades and the limitations associated with each.

Most sample holders cannot be used in a single use fashion because of their high cost. Accordingly, they must be carefully cleaned, typically with organic solvents, after each analysis to prevent contamination from one sample to the next. The high cost of sample holders tends to inhibit long-term retention of mounted samples.

A sample cell that is easy to use, is insensitive to or non-reactive with liquid samples or solvents, and has a spectral range useful for most routine analyses is described in the aforementioned U.S. Pat. No. 5,470,757. There, a microporous film is used as a support for liquid samples. Other approaches have been described in U.S. Pat. Nos. 5,290,705 and 5,453,252.

X-ray fluorometry sample holders adapted so as to retain samples in a predetermined portion of a filter medium are described in U.S. Pat. No. 4,405,560 and 4,562,045. There, portions of a filter medium are isolated from the remainder of the medium by providing slits that essentially surround the predetermined portion. The small pieces of the filter medium that connect the isolated portion from the remainder of the filter medium can be impregnated with paraffin to prevent sample applied to the isolated portion from migrating into the remainder of the filter medium. The use of paraffin as a confining means and the relatively thick filter medium required (approximately 200 μm thick) prevent this type of sample holder from being used for quantitative measurements, especially where transmission and/or absorption measurements are to be made or where organic liquid-contining samples are to be analyzed (because of the solubility of the paraffin).

SUMMARY OF THE INVENTION

In brief summary, the present invention provides a device for holding a sample to be spectroscopically analyzed (i.e., a sample holder) that includes a) porous means for receiving the sample; and
b) in and/or on the receiving means, means for confining the sample within a predetermined portion of the receiving means. This confining means is non-porous, and it surrounds and defines the predetermined portion of the receiving means.

The sample holder also can include a frame which can provide a convenient, easy means to handle the device. When present, the frame includes upper and lower surfaces as well as one or more apertures extending theretrough (i.e., from the upper surface to and through the lower surface). Extending across the aperture(s) and held within the frame is the aforementioned receiving means.

In another aspect, the present invention provides a method of spectroscopically analyzing a sample comprising the steps of transmitting radiation through a sample that has been applied to the receiving means of the above-described sample holder (and optionally allowed or caused to dry) and analyzing the radiation transmitted through the sample and the receiving means. A preferred type of spectroscopic analysis is IR spectroscopy.

The sample holder of the present invention can be used in manual and automated transmission spectroscopic analysis, is simple to use, permits simplified sample preparation, and provides precise and accurate spectra of samples. It can be sufficiently inexpensive to be discarded or stored after a single use. It also can eliminate the need for sample clean up and post-analysis reconditioning of the sample holder, which provides improved safety (particularly in cases of hazardous samples and/or cleaning agents) as well as greater convenience and time economy. Certain embodiments of the sample holder of the present invention are essentially inert toward a sample applied thereto and exhibit minimal substrate absorbances or artifacts so as not to interfere with the spectra obtained.

In the present invention, the receiving means portion of the sample holder can be a screen such as that described in U.S. Pat. No. 5,453,252, a microporous sheet such as that described in U.S. Pat. No. 5,470,757, or any other essentially planar material that is capable of retaining a sample applied thereto. However, relative to the sample holders described in the two references just mentioned, the sample holder of the present invention has the distinct advantage of being useful for quantitative analyses. This is due to the inclusion of a means to confine a measured volume of the sample within or on the surface of a predetermined, defined portion of the sample receiving means.

The sample holder of the present invention facilitates the handling of samples to be spectroscopically analyzed.

Although most of the discussion herein is directed to IR spectroscopy, the sample holder of the present invention can also be used in a variety of spectrophotometers (e.g., UV-visible, near IR, far IR, X-ray fluorescence, X-ray diffraction, fluorescence, and Raman). Because of certain characteristics inherent in the receiving and confining means, the sample holder of the present invention is especially well suited for transmission and absorption spectroscopy techniques.

Unless a contrary intention is indicated, the following definitions apply herein:

"average characteristic width" means the average of the largest of the cross-sectional dimension of the pores, which is the pore diameter if the pores are substantially circular in cross-section;

"quantitative" means the ability to obtain reproducible measurements of both the identity and amount of a given material in a known amount of sample;

"microporous" means having pores with an average characteristic width of about 0.1 to about 50 µm;

"transmittance (T)" is the ratio (expressed in percent) of the power of radiation received at the spectrophotometer detector to the power of radiation incident on the sample;

"absorbance (A)" is the negative of the logarithm of the transmittance value (i.e., $A = -\log_{10} T$); and "absorptivity" means the inherent property of a chemical compound that determines the amount of incident light absorbed at a given frequency.

BRIEF DESCRIPTION OF DRAWING

Further explanation of the invention can be obtained by reference to the drawings. These drawings, which are idealized and not necessarily to scale, are intended to be illustrative and should not be used to unduly limit the invention.

FIG. 1 is a plan view of one face of one embodiment of the sample holder of the present invention.

FIG. 2 is a plan view of one face of an embodiment of the sample holder of the present invention in which two samples can be held simultaneously.

FIG. 3 is a plan view of one face of another embodiment of a sample holder of the present invention in which the holder is in the form of a disk.

FIG. 5 is a plan view of one face of an embodiment of the sample holder of the present invention in which the sample holder is not surrounded by a frame.

FIGS. 6a–6e are is a greatly enlarged cross-sectional view of five embodiments of the sample receiving means of the sample holder of the present invention.

DETAILED DESCRIPTION OF ILLUSTRATIVE EMBODIMENTS

Figure 4:
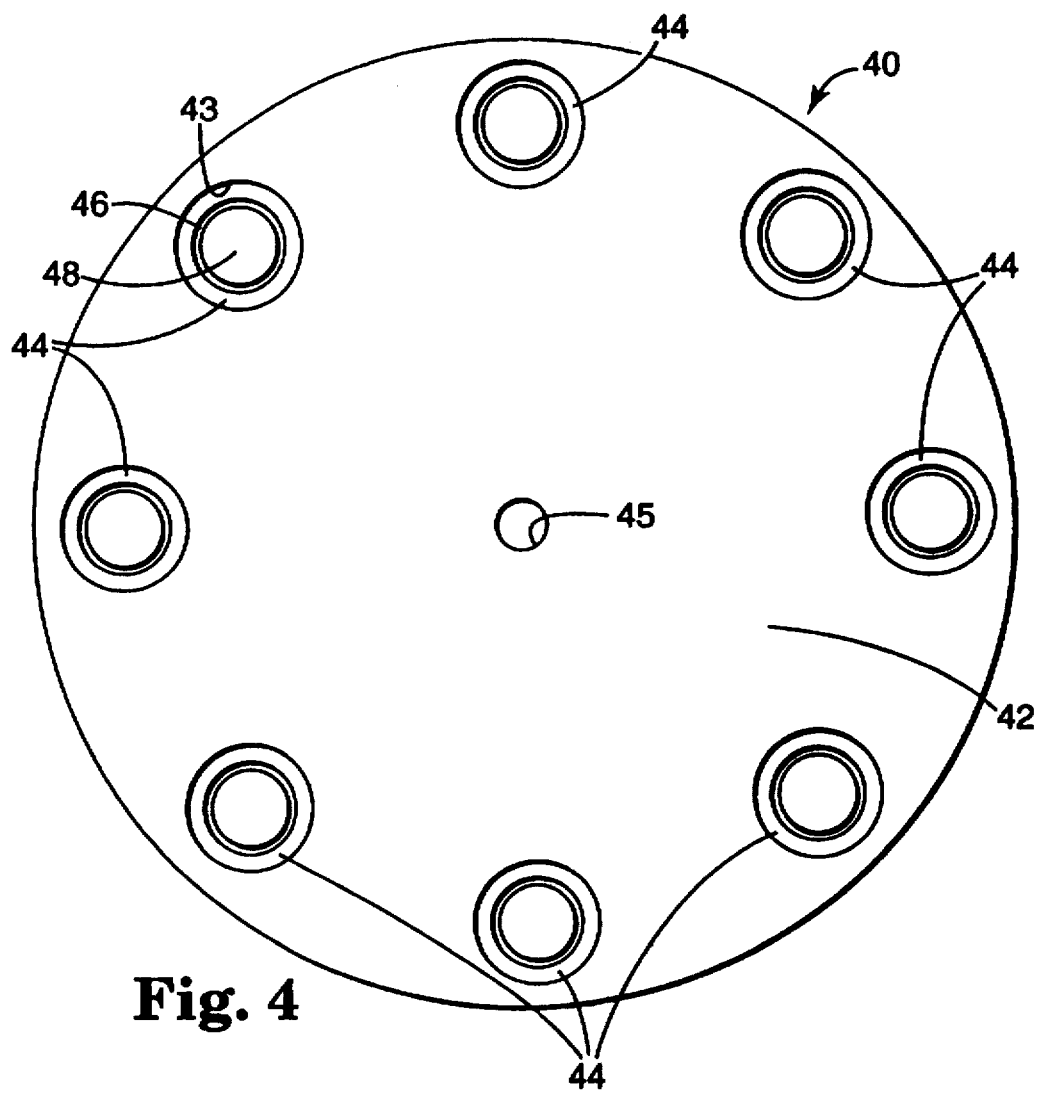
FIG. 4 is a plan view of another embodiment of the sample holder of the present invention in which numerous samples can be held simultaneously and analyzed sequentially.

FIG. 1 illustrates sample holder 10 that includes frame 12 and sample receiving means 14. Sample receiving means 14 covers aperture 13 extending from the top surface to the bottom surface of frame 12. Frame 12, which preferably is substantially flat and rigid, acts as means for mounting sample holder in a spectrophotometer.

Frame 12 can be constructed from a variety of materials, including, but not limited to, paper, cardboard, paperboard, polish stock calendered chipboard, plastic (e.g., polypropylene) sheet stock, pressure sensitive adhesive tapes, metals, metal alloys, ceramics, composites, elastomers, and glass. Preferred materials include paperboard, polished stock calendered chipboard, and plastic sheet stock. Often, frame 12 consists of two identically shaped pieces having at least one opening extending from the top surface(s) to the bottom surface(s), joined such that receiving means 14 is fixed between the two pieces and extends across aperture 13 in frame 12.

The two pieces can be joined together by any of a number of means appropriate to the material from which they are made, including, but not limited to, adhesive (e.g., liquid, hot melt, pressure sensitive), double-sided pressure sensitive adhesive tape, welding (e.g., sonic, spot, solder, arc, thermal, etc.), radio frequency (RF) sealing, crimping, mechanical fastening or compression, and substantial equivalents thereof A standard photographic 35 mm slide mount can be used as frame 12 for sample holder 10. Slide mounts, which are typically made of plastic or paperboard, are readily available, can accommodate and hold flat receiving means 14, are sufficiently rigid, and fit easily into the sample holder mount of spectroscopic instruments. An advantage of some commercially available photographic slide mounts is that they possess adhesive, mechanical, or a combination of adhesive and mechanical mounting.

In some instances, a spectroscopist might wish to archive or store a sample for future reference. Accordingly, frame 12 preferably is constructed of a material that can be written on or otherwise labeled so that pertinent information relating to the sample (e.g., sample or index number) can be noted thereon. Alternatively, a label or other additional information bearing media (e.g., microfilm, magnetic media, bar code, etc.), can be included on frame 12 if desired.

In some embodiments, sample holder 10 can further comprise a protective cover or flap (not shown) that covers the aperture during storage and is moved clear of the beam path during spectroscopic analysis. Alternatively, a protective cover that is transparent to IR light (or is non-absorptive at the wavelength(s) of interest) can be used and need not be removed from the beam path during analysis.

The size and shape of frame 12 is dependent in part upon the sample cell receptacle of the particular spectroscopic instrument(s) in which sample holder 10 is to be used. Currently, spectroscopists typically use sample holders that are about two inches (i.e., about 5 cm) wide.

Receiving means 14 is illustrated as a screen with a regular grid pattern, although a non-uniform grid pattern can also be used. Although receiving means 14 is illustrated in sample holder 10 as a screen, other forms also can be used. These are discussed in detail below in the discussion of other embodiments of the sample holder of the present invention.

With a regular grid pattern screen (e.g., the type used in window screens), the openings are regular in shape and have uniform cross-sectional areas of a size such that the sample is retained on the screen by the surface tension of the sample. Useful cross-sectional areas of the grid openings range from about 0.1 to about 1.5 $mm^2$, with those having cross-sectional areas of about 1 $mm^2$ being preferred. Non-uniform grid patterns include random, graded change, chaotic mesh (e.g., that present in steel or glass wool), non-woven scrims, etc. A complete description of such non-uniform grid patterns can be found in U.S. Pat. No. 5,453,252 (see, especially, FIG. 4 and the accompanying text, both of which are incorporated herein by reference). Each of these patterns is within the scope of screens useful as a receiving means in the sample holder of the present invention.

The fibers of a screen used as receiving means 14 can be made from a variety of materials including glass, quartz, metals, alloys, as well as polymeric materials such as nylons, polyethylenes, polystyrenes, fluoropolymers (e.g., polytetrafluoroethylene), polyamides, polyaramids, polybutadiene, etc. Where the fiber is made from an essentially inflexible material (e.g., glass or quartz), the fiber preferably is coated with a flexible polymer such as poly (vinyl chloride).

Included in receiving means 14 is sample confining means 16. In this particular embodiment, sample confining means 16 is illustrated as a ring of non-porous material that has been deposited on or impregnated into receiving means 14. Examples of useful non-porous materials include cyanoacrylate-type liquid adhesives, silicone adhesives, hot melt-type viscous liquid adhesives, paints, epoxies, and other hardenable materials. Such materials can be deposited in their liquid form onto receiving means 14 and allowed to penetrate into the screen or mesh. On hardening, the materials form a non-porous barrier within receiving means 14. Alternatively, an inert liquid, such as a silicone polymer or a fluoropolymer capable of penetrating into the screen or mesh of receiving means 14 can be applied in a desired pattern (typically, a circle) to form an impenetrable barrier. Inert liquids useful in this manner preferably have sufficient viscosity to remain in place and are not reactive with, soluble in, solubilizing toward, or swellable in a sample applied to receiving means 14.

Confining means 16 preferably is spaced away from the edge of aperture 13 so that a sample applied to receiving means 14 remains in sampling platform 18, and does not contact any portion of frame 12. By retaining all sample in sampling platform 18, sample holder 10 can be used for quantitative spectroscopic measurements as described below.

Although aperture 13 and confining means 16 are illustrated as circular, both aperture 13 and confining means 16 can be of any shape such as, for example, square, rectangular, triangular, polygonal, and irregular. Aperture 13 need not be the same shape as confining means 16.

Sampling platform 18 constitutes a sample-retaining area, the perimeter of which is defined by confining means 16. The size of sampling platform 18 can be varied as long as its diameter is wide enough to accommodate the beam path of the spectrophotometer. Preferably, sampling platform 18 has a diameter that is greater than that of the incident IR beam. Typically, IR spectro-photometers use a target area of from about 5 mm to about 15 mm wide. Thus, sampling platform 18 can have a diameter greater than about 5 mm up to a practical limit based on the spectrophotometer sample area and the sample size. For reasons of instrument size limitations, the size (area) of sampling platform 18 typically ranges from less than 1 to about 6 $cm^2$ per each face.

If desired, larger or smaller sampling platforms can be used in accordance with the invention. The increase in sensitivity of modern instruments enables the taking of spectra of very small samples; therefore, sampling platform 18 can be very small. IR microscopes, such as the Nic-Plan™ IR microscope (Nicolet Instrument Corp.; Madison, Wis.), are available. In such instruments, sampling platform 18 can have a diameter as small as 3 µm, more typically about 100 µm.

FIG. 2 illustrates sample holder 20 that includes frame 22 and two sample receiving means 24. Sample receiving means 24 cover two apertures 23 extending from the top surface to the bottom surface of frame 22. Frame 22 can be made from the same materials and constructed in the same fashion as described previously with respect to FIG. 1.

Receiving means 24 are illustrated as microporous sheets, although other forms (including the previously described screen) also can be used. Where a microporous sheet is used, it is preferably inert toward (i.e., non-reactive with and insoluble in) any sample to be applied thereto, including any solvents that such samples might contain.

The microporous sheet preferably is very thin because thicker sheets tend to lead to greater interference due to their stronger spectral absorbances. Typically, useful polyethylene microporous sheets have a thickness of less than about 150 µm, preferably about 25 to about 150 µm, more preferably about 125 µm, and a basis weight between about 1.0 and 90 $g/m^2$.

Typically, the pore density of microporous sheets used as receiving means 24 is such that the void volume, as measured by ASTM D4197-82, is greater than about 20%, preferably in the range of about 50 to about 98%, more preferably between about 75 and about 90%. In general, the greater the void volume, the greater the amount of sample in the beam path (which improves spectroscopic accuracy), the less likely inherent absorbances of the sheet are to interfere with analysis of the response of the sample, and the more readily solvent evaporates from a sample applied to the sheet. Many useful microporous polymer sheets are open structures wherein only a fraction of the total volume is occupied by the polymer material; thus, a greater portion of the matter in the beam path is the sample itself.

Conventional non-microporous films are typically less useful and, in many instances, inoperable for use herein. Samples applied to such sheets fail to effectively wet the surface of the film and, as a result, the sample beads and tends to run off the film when mounted in the spectrophotometer. However, when those same samples are applied to microporous sheets made from the same polymers, the samples tend to wick into the pores of the sheet, enabling the sample to be spectroscopically analyzed. If the sample is analyzed quickly after application to the sample holder, such as by FT-IR, the solvent portion of the sample can be spectroscopically analyzed. Alternatively, the sample can be retained for a time to permit the solvent portion to evaporate, leaving the less volatile portion deposited on the sample holder for subsequent analysis.

As described in U.S. Pat. No. 5,470,757, the disclosure of which is incorporated herein by reference, where a microporous sheet is used as sample receiving means 24, analysis of, for example, aqueous samples and biological fluids can be facilitated. Although such samples can be applied directly to sampling platforms 28, preferably a cosolvent (e.g., methanol) is first applied thereto so as to wet them, making them more receptive to the sample. Water and cosolvent can then be evaporated as previously described. For many water-based samples such as primers and adhesives (e.g., those that contain a surfactant), wetting often is not necessary. With either of these procedures, spectra of water-based materials can be readily obtained without the use of expensive equipment such as ATR cells or resorting to other tedious sample preparation techniques.

Hydrophilic porous films (e.g., cellulose, paper, nylon-6, nylon-66, poly(vinyl alcohol, etc.) have been found to be useful as receiving means 24 where aqueous samples are to be spectroscopically analyzed. Samples can be applied directly to the film without a need for the previously described wetting. In addition to analysis of aqueous samples, hydrophilic porous films can be useful in the analysis of biological fluids such as blood, sweat, tears, urine, semen, etc. Such samples can be applied directly to sampling platforms 28 without the need for lengthy sample preparation, and clear, distinct spectra can be obtained. Microporous sheets made of materials that are inherently hydrophilic (e.g. cellulose, nylon-6, nylon-66, or poly(vinyl alcohol)) or that are treated to render them hydrophilic (e.g., by coating with suitable material or applying suitable treatment) can be used herein.

Microporous polymer sheets can have a plurality of interconnecting microscopic pores opening through at least one face of the sheet. The pores can open through only one or both faces of the sheet. In the event they open through only one surface, the sample preferably is placed on that surface. Preferably the pore size distribution across the microporous sheet, particularly across sampling platforms 28, is substantially uniform so as to provide a low sheet transmittance variability. Pore sizes typically range from about 0.1 to about 50 µm in their average characteristic width. Sheets with uniform, substantially circular pores formed by, for example, laser ablation, sheets made of fibrillated masses with openings of varying size and configuration, sheets made of non-woven materials, and sheets made of strands having uniform diameter of material defining a tortuous path (e.g., random or fixed) through the sheet each can be useful as receiving means 24.

As used herein, "microporous sheets" includes polymeric sheets having at least one structured surface wherein the surface has surface voids, grooves, depressions, etc., having a minimum depth of about 0.1 µm and a minimum width of about 0.1 µm therein, typically having an average characteristic dimension (i.e., the average of the largest dimension of the structure element in a plane parallel to the aperture of the sample holder) of at least between about 0.1 and about 50 µm, sometimes even substantially larger. Such sheets can be formed from solid polymeric sheets by a variety of surface modifying and replication techniques including, but not limited to, laser ablation, molding, embossing, and extrusion. Such surface features can increase the ability of the sample holder to retain sample material, especially particulate materials. Structured surface features may also be formed on microporous sheets having a plurality of pores as described above.

Composite sheets comprising a base sheet (e.g. a microporous sheet as described above) bonded to an open mesh also can be used. The mesh facilitates collection and retention of sample material. The base sheet supports the sample material in the aperture. The composite sheet must meet the transmittance criteria described herein but, because the mesh is open, the bulk properties of the mesh need not meet those transmittance criteria.

U.S. Pat. No. 4,539,256 discloses microporous sheet materials and methods for making same, many of which can be used in sample holders of the invention. Various patents assigned to W. L. Gore and Associates, Inc. (Wilmington, Del.), including U.S. Pat. Nos. 3,953,566, 3,962,153, 4,096,227, 4,110,392, 4,187,390, and 4,194,041, describe the preparation of porous articles, including microporous sheets, from polytetrafluoroethylene (PTFE). Many of the polymeric sheet materials described in those patents also can be used in accordance with the present invention.

Many types of microporous polymer sheets useful in some embodiments of the invention, in a variety of polymers, thicknesses, and void volumes are commercially available. Among these are Celgard™ hydrophobic or hydrophilic microporous polyethylene or polypropylene films (Hoechst Celanese; Charlotte, NC), GORE-TEX™ microporous PTFE films (W. L. Gore), Zitex™ microporous PTFE films (Norton Performance Plastics; Wayne, N.J.), and Durapore™ microporous hydrophilic films (Millipore Products Division; Bedford, Mass.). Other illustrative examples include microporous sheets of polyolefins (e.g., polyethylene, polypropylene, and copoly(ethylene-propylene)), poly(vinylidene fluoride), polyester, polycarbonate, cellulose acetate, cellulose nitrate, poly (vinyl chloride), and nylon. The sheet can consist essentially of one or more of the chosen polymeric films. The sheet can comprise special agents (e.g., hydrophilic or hydrophobic coatings) or can be surface treated, as discussed below.

When microporous sheets are used as receiving means 24, a preferred sheet material is microporous polyethylene. Polyethylene is inert toward many chemicals, is insensitive to moisture, and provides strong (e.g., tear and puncture resistant) films at low thicknesses. Except for the region of about 3000 to about 2800 cm$^{-1}$ where its aliphatic carbon-hydrogen (C—H) bond stretching is evident as strong absorbances (i.e., 2918 and 2849 cm$^{-1}$), polyethylene can be used across the IR range of about 4000 to about 200 cm$^{-1}$. Polyethylene exhibits a limited number of other signals in other portions of the range (e.g., 1465 and 721 cm$^{-1}$), but these are typically narrow, well-defined, low intensity absorbances that are easily taken into account. (Polyethylene having substantial crystallinity has two additional absorbances caused by the splitting of the latter two absorbances into pairs of peaks.) Preferably, microporous polyethylene used in to make microporous sheets is prepared according to the teaching of U.S. Pat. No. 4,534,256, which process is incorporated herein by reference.

Another useful polymer, particularly where the aliphatic C—H bond stretching region is of significant interest, is microporous PTFE. This material has no absorbances above about 1500 cm$^{-1}$, so the aliphatic C—H stretching region (about 3000 to about 2800 cm$^{-1}$) is free of interfering absorbances. Sheets made from PTFE (as well as polymers and copolymers of chlorotrifluoroethylene) can be useful in the range of about 4000 to about 200 cm$^{-1}$.

Although a wide variety of microporous polymeric sheets are useful, other porous sheet materials can also be used. These include, for instance, paper, nonwoven polymeric films, fiberglass, spun glass, glass cloth, inorganic membranes (including ceramics), woven fabrics, knit fabrics, and other fibrous sheet materials. The sheet preferably is made from a material selected to reduce spectral interference of the inherent absorbances of the porous sheet with the bands being analyzed in the sample. Although each material has characteristic absorbances, the absorbances are preferably in regions of the IR spectrum that do not interfere with the absorbances of the sample. In other words, the porous sheet preferably exhibits relatively low absorbance (i.e., is highly transmissive) in the spectral region(s) of interest.

The preference for low absorbance sheet materials can be somewhat lessened through the use of modern spectroscopic instruments that have the capacity to subtract background absorbances due to solvent(s), the cell, the atmosphere, etc. In a dispersive type instrument, the IR beam is split into two parallel beams, one through the sample, and the second, or reference beam, through a blank cell. When taking a spectrum of a solvated sample, a cell containing only pure solvent is placed in the reference beam so that the instrument can subtract the spectrum of the solvent from that of the dissolved sample. In FT-IR spectrophotometers, the spectrum of the background of a blank (or reference) cell can be scanned and electronically stored so that it can be subtracted from sample spectra collected later.

The process of subtraction of background absorbances, which can be imperfect with conventional sample holders, can also be imperfect with the sample holder of the present invention. This is due to the fact that absorbances are not always cleanly subtracted and, therefore, interfere with the absorbances of the sample, particularly when the sample exhibits subtle absorbances that can be inadvertently masked or lost by the subtraction process. Accordingly, the microporous sheet is preferably selected to minimize, and more preferably eliminate, interference of the absorbances of the microporous sheet with the sample. As the IR spectra of many polymer films are widely known, choosing an appropriate sheet for use in accordance with the present invention is well within the capability of one of ordinary skill in the field of spectroscopy.

Selection of a sheet for a particular application depends in part on the composition of the sample and analysis to be performed thereon. Microporous sheets can be evaluated for use in particular applications in accordance with the invention by measuring the baseline transmittance or absorbance of the sheet. Polymeric films typically scatter a portion of the light incident thereto. In a sample holder of the present invention in which a microporous sheet is used as receiving means 24, the average baseline of the microporous sheet in the range of about 4000 to about 400 cm$^{-1}$ preferably is greater than about 1% transmittance, more preferably greater than about 10% transmittance, most preferably greater than about 50% transmittance. Expressed in terms of absorbance units, the sheet preferably has an absorbance at the wavelength(s) of interest of less than about 2, more preferably less than about 1, most preferably less than about 0.3. The average baseline absorbance of a sheet is readily determined by obtaining the absorbance of the background (i.e., empty sample holder with no sheet) and the absorbance of subject sheet at about 4000 cm$^{-1}$ and about 400 cm$^{-1}$. The aperture for both the background and sheet absorbances should have equivalent dimensions. The background absorbances are subtracted from those of the sheet at about 4000 cm$^{-1}$ and about 400 cm$^{-1}$, respectively, and the resultant values are then added together and divided by two to obtain the average baseline absorbance.

A microporous polymer sheet can be treated to improve sample collection and retention properties. Depending upon the sheet material, treatment, and intended sample, the sheet can be treated prior to or during fabrication of the sample holder, or at later time prior to application or collection of the sample material.

In another embodiment, at least a portion of the surface of the sheet is treated by application of a material that modifies the interaction of the sheet with the desired sample material (e.g., coating or graft polymerization). For example, azlactone materials can be used to concentrate proteins in solution on a sample holder for IR spectroscopic analysis. See, e.g., U.S. Pat. No. 5,344,701.

Also included in sample holder 20 are sample confining means 26. In this particular embodiment, sample confining means 26 are illustrated as annular compressions in receiving means 24. These compressions can be achieved by, for example, embossing a microporous sheet so as to form a compressed area which is non-porous. This embossing can be accomplished via die stamping performed manually, with a hydraulic press, or by some other similar means.

Confining means 26 encircle and define sampling platforms 28. Any sample placed within the perimeters defined by confining means 26 remains in sampling platforms 28. This allows for quantitative measurements of such samples. Confining means 26 preferably are spaced away from the edges of apertures 23 so that any samples applied to sampling platforms 28 do not contact any portion of frame 22.

Although apertures 23 and confining means 26 are illustrated as circular in sample holder 20, both apertures 23 and confining means 26 can be of any shape, as described previously. Apertures 23 need not be the same shape as confining means 26.

Although not apparent in FIG. 2, the compressions that make up confining means 26 can be on the side of receiving means 24 opposite that which is shown, which assists in confining the sample applied to sampling platforms 28. (See discussion infra.)

FIG. 3 illustrates sample holder 30 that includes circular frame 32 with aperture 33 and sample receiving means 34. Sample holder 30 is in the form of a disk (or coin), as might be used with, for example, a multisample analysis system (Pike Technologies; Madison, Wis.). Although sample receiving means 34 again is depicted as a microporous sheet, other forms, including the previously described screen, can be used.

On/in receiving means 34 is sample confining means 36. Again, sample confining means is portrayed as an annular compression of the microporous sheet that makes up receiving means 34. The annular compression can be formed in receiving means 34 by the same procedures described previously.

Confining means 36 encircles and defines sampling platform 38. Any sample placed within the perimeter defined by confining means 36 remains in sampling platform 38. This allows for quantitative measurements of such a sample. Confining means 36 preferably is spaced away from the edge of aperture 33 so that a sample applied to sampling platform 38 does not contact any portion of frame 32.

FIG. 4 illustrates sample holder 40 that includes circular frame 42, apertures 43, a central hole 45, and multiple receiving means 44. This type of construction can be used to hold a series of samples as might be used with a Model 710 FT-IR spectrophotometer (Nicolet Instruments; Madison, Wis.) equipped with a Model 0084-1XX or Model 0084-2XX sample wheel (SpectraTech, Inc.; Shelton, Conn.). (Central hole 45 allows sample holder 40 to be mounted on the rotatable spindle of such an instrument so that each sampling platform 48 can be rotated into the line of the IR beam produced by the spectrophotometer.) Although sample receiving means 44 are portrayed as microporous sheets, other forms (including the previously described screen) can be used.

On/in receiving means 44 are sample confining means 46. Again, sample confining means 46 are portrayed as annular compressions of the microporous sheets that make up receiving means 44. The compressions can be formed in receiving means 44 by the same process(es) described previously.

Confining means 46 encircle and define sampling platforms 48. Any samples placed within the perimeters defined by confining means 46 remain in sampling platforms 48. This allows for quantitative measurements of such samples. Confining means 46 preferably are spaced away from the edges of apertures 43 so that a sample applied to sampling platforms 48 does not contact any portion of frame 42.

FIG. 5 illustrates sample holder 50 which includes receiving means 54, confining means 56, and sample platform 58. In this embodiment, sample confining means 56 again is portrayed as an annular compression in the microporous sheet that makes up receiving means 54. The compression can be formed in receiving means 54 by the same processes described previously.

Confining means 56 encircles and defines sampling platform 58. Any sample placed within the perimeter defined by confining means 56 remains in sampling platform 58. This allows for quantitative measurements of such a sample.

Optional adhesive 55 can be coated on one or more sides and faces of receiving means 54 to allow sample holder 50 to be releasably mounted in the light beam (not shown) of a spectrophotometer (not shown). Adhesive 55 can be repositionable, non-outgassing, etc.; those skilled in the art can readily identify and select many suitable adhesives for a variety of desired applications (e.g., heat-activated, particular tack characteristics, etc.). Adhesive 55 can be any of the pressure sensitive adhesives mentioned previously.

Adhesive 55 is optional because one can envision a roll that comprises a series of sample holders that can be sequentially passed before an incident beam and taken up on collecting spool. In such a configuration, adhesive 55 would be unnecessary.

Figure 6A:
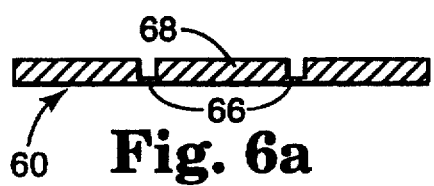
Figure 6B:
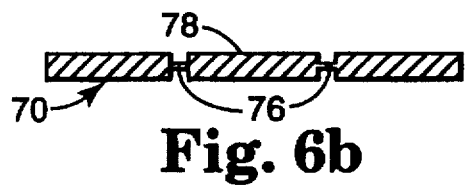
Figure 6C:
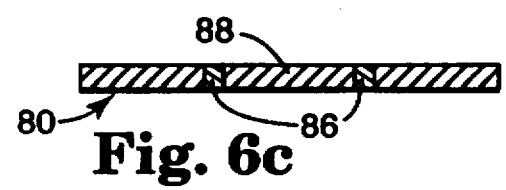

FIG. 6 is a greatly enlarged, cross-sectional view of five embodiments of a sample retaining means of the sample holder of the present invention. In FIGS. 6a, 6b, 6c, 6d and 6e, sample receiving means 60, 70, 80, 90 and 100 (respectively) are microporous membranes, as described above.

In FIG. 6a, microporous membrane 60 has been compressed so that confining means 66 is an annular compression. Confining means 66 defines the perimeter of sample platform 68. When a liquid sample is placed on sample platform 68, it soaks therethrough but does not migrate into the bulk of microporous membrane 60 (because of the lack of porosity of the compressed area defined by confining means 66). Confining means 66 can be formed by placing microporous membrane 60 on a platen and striking the membrane with a circular die.

In FIG. 6b, microporous membrane 70 has been compressed so that confining means 76 again is an annular compression. Confining a means 76 defines the perimeter of sample platform 78. When a liquid sample is placed on sample platform 78, it soaks therethrough but does not migrate into the bulk of microporous membrane 70. Confining means 76 can be formed by striking microporous membrane 70 with identical circular dies (from above and below).

In FIG. 6c, microporous membrane 80 has had a ring of a liquid applied to the top surface thereof, with the liquid having soaked through microporous membrane 80 and subsequently hardened so as to form annular confining means 86. Confining means 86 defines the perimeter of sample platform 88. When a liquid sample is placed on sample platform 88, it soaks therethrough but does not migrate into the bulk of microporous membrane 80 (because of the impenetrable nature of confining means 86).

In FIG. 6d, a solid, nonporous ring 99 (shown in cross-section) lies atop microporous membrane 90 and is affixed thereto by an adhesive that has been applied to membrane 90 and has penetrated therethrough to form confining means 96 (here an annular barrier). Confining means 96 defines the perimeter of sample platform 98. Where a liquid sample placed on sample platform 98 penetrates thereinto only partially, the nonpenetrating portion thereof is retained by solid ring 99. If the liquid sample does not penetrate into sample platform 98 at all (which can occur for a variety of reasons including sample viscosity, a significant difference between the surface energy of the sample platform and the surface tension of the liquid sample (including any solvent, when present), and the use of a relatively dense, nonporous membrane as the receiving means, providing that the sampling platform is sufficiently transparent to radiation used in the analysis or that a reflective analytical technique such as X-ray fluorometry is used), solid ring 99 defines the area and volume of sample that this sample retaining means is capable of retaining for analysis (i.e., ring 99 acts as the confining means). Ring 99 can be any solid, nonporous material that can be adhered to membrane 90 such that it does not interfere with any subsequent IR analysis. Suitable materials can include metal, wood, glass, plastic, ceramic, composites, nonporous polymers, and the like.

In FIG. 6e, microporous membrane 100 has been treated with an excess of a hardenable liquid such that the liquid has penetrated into membrane 100 to form, on hardening, annular confining means 106. In addition, the excess liquid has hardened to form a protrusion 109 above the plane of membrane 100. Confining means 106 defines the perimeter of sample platform 108. Certain liquid samples placed on sample platform 108 might penetrate thereinto slowly or only partially, the nonpenetrating portion thereof being retained by protrusion 109. If a liquid sample does not penetrate into sample platform 108 at all, protrusion 109 defines the area and volume of sample that this embodiment is capable of retaining for analysis. Suitable hardenable liquids include hot melt adhesives, viscous adhesives, thermosetting liquid polymers, and the like.

Regardless of the particular shape of the sample holder of the present invention, samples are applied to the sampling platform(s) thereof in a simple manner. Although neat samples can be applied directly to a sample holder, more commonly a sample that has been dissolved in solvent is used to facilitate handling. Samples that have been solvated in an organic liquid readily wet the surface of the screen or microporous sheet (with little or no swelling of the polymer matrix of such a sheet), and solvent quickly evaporates from the surface thereof Typically, any solvent used evaporates within 10 to 30 seconds. This can be accelerated by exposing the sample to an external heat source, such as a heat lamp, for a few seconds after application of the sample to the holder. (See, e.g., European Pat. No. 478,596.) Sample holders comprising sheets having pores that open through both surfaces, extending all the way through the sheet (even when such pores constitute a tortuous path through the sheet), can optimize this effect. After the solvent has been evaporated, the sample holder can be mounted in a spectrophotometer.

To achieve quantitative analysis using the sample holder of the present invention, precisely the same amount of sample in each procedure or IR scan needs to be analyzed each time. Therefore, any method that allows the same amount of sample to be applied to the sampling platforms, as defined by the confining means, can be used. In many instances, a precise amount of sample to be analyzed can be applied directly to the sampling platform using a variety of pipettes. In some analyses, the sample to be analyzed does not readily wet the sampling platform, and use of a micropipette by itself can be prohibitively slow. In such cases, it has been found that a precise amount of a viscous sample can be applied to a brass button (with a smooth upper surface) of approximately the same diameter as the sampling platform, after which the sampling platform is held firmly in place (by hand or any other suitable means) on the sample for a sufficient time to allow the sample to soak into the sampling platform.

Use of sample holders of the present invention allows for quantitative, as well as qualitative, analysis of samples. Since the spectrum of any sample is a function of Beer's Law, the intensity of any peak (measured by peak height or area, total absorbance, or total transmittance) is a linear function of the amount of sample present. Given the extinction coefficient for a particular peak or absorbance in a sample, the amount of sample present can be calculated. Alternatively, a series of samples can be prepared varying the loading, e.g., amount or concentration, of a sample. The intensities of preselected absorbances can be plotted as a function of the loading, and the concentration of an unknown sample can then be determined by comparison with the plotted data. This is especially useful in the analysis of mixtures, where the concentration of a species in the mixture can be determined by the comparison of the relative peak heights of the constituents. For example, the relative amounts of saturated and unsaturated fats in edible oils can be easily determined by comparing C—H absorbances at 3010 and 2854 cm$^{-1}$ as disclosed by Afran and Newbery in SPECTROSCOPY, 6(1), pp. 31-33 (1990), without resorting to ATR sample holders.

Sample holders of the present invention allow for efficient and simplified quantitative analysis of samples. Absorption of impinged IR energy by a sample is measured indirectly by the spectrometer and typically reported as percent transmittance, T, where $$T=100 \times P_{sample}/P_{background}$$

in which $P_{sample}$ is the intensity of light reaching the detector in the spectrometer and $P_{background}$ is the light intensity as measured in the absence of a sample. For analysis, transmittance is converted to absorbance, A, where $$A=\log_{10}(1/T)$$

The intensity of the absorbance of a functional group can be directly related to the concentration of that functional group, making quantitative measurements possible based upon the fundamental relationship between absorbance, absorptivity, and concentration expressed by Beer's Law. See, e.g., G. W. Ewing, *Instrumental Methods of Chemical Analysis*, 5th ed., pp. 32-35 (McGraw-Hill, New York, 1985), incorporated herein by reference. Since absorptivity is an inherent property of each chemical compound, it is a constant for a given compound at a given wavelength. Sample holders of the present invention comprise sampling platforms of microporous sheets having essentially uniform thickness (typically about 125 µm) and, therefore, a uniform volume. Thus, for a set of similar samples, a calibration curve can be generated relating IR absorbance (i.e., peak height or area) directly to the concentration of a given component.

Since absorbance is directly proportional to concentration, differences in absorbance (e.g., between that of the sample and that of the background) are most readily observable when sample concentration is high relative to the background (i.e., sampling platform). Therefore, the sensitivity of the method of the invention depends on the use of a sample of sufficient size so that sample absorbances are observable after background absorbances are subtracted out but not so great so as to exceed the capacity of the detector.

An illustrative example is the use of FT-IR for quantitative analysis of motor oil contaminated through engine wear or malfunction (e.g., leakage of coolant or exhaust into the motor oil). FT-IR methods are well-suited for such analysis, since the spectra of new/unused oils can be taken and stored in computer memory to be retrieved for spectral subtraction once a spectrum is taken of used/contaminated oil. The spectra of the new and used oils are generally quite similar, and subtracting the spectrum of the new oil from that of the used oil results in a spectrum in which only the differences between the oils are seen. Differences represent products formed by, for example, oxidation of base oil, potential contaminants, and/or depletion of additives. In a spectrum of only the used oil, small differences might be difficult to see and even more difficult to quantify. New oil reference spectrum subtraction allows useful information to be emphasized in an otherwise complex combination of spectral features.

Sample holders of the present invention can also be used for tandem filtration/IR analysis. Some of the microporous films used herein as sheets are known to be useful as filtration media. See for example Prasad et al., "Nondispersive Solvent Extraction Using Microporous Membranes, New Membrane Materials and Processes for Separation," AIChE Symposium Series No. 261, vol. 84, pp. 42-53 (1988) and Baker et al., "Membrane Separation Systems—A Research and Development Needs Assessment," Final Report, vol. 2, U.S. Dept. of Energy, Office of Program Analysis (April 1990). In this technique two sample holders are positioned, each disposed horizontally, one over the other. A sample containing an insoluble fraction is then applied to the exposed sheet of the top sample holder. If desired, a spectrum of this starting material can be obtained. A portion of a suitable solvent is then applied to the sample, dissolving the soluble fraction(s) and washing it through the top sample holder onto the bottom sample holder. The insoluble fraction thus is filtered out of the sample by the top sample holder, on which it may subsequently be spectroscopically analyzed, and the soluble fraction is collected on the bottom sample holder, on which it can be spectroscopically analyzed following evaporation of the solvent.

A variation of this technique also allows for the analysis of soluble materials from surfaces. By this technique, a sample holder may be placed on the surface of a solid object. Solvent is then applied so that the solvent is in contact with both the surface and the sample holder. The soluble materials from the surface will be extracted onto the surface of the sheet. The solvent can then be evaporated and the sample spectroscopically analyzed.

An advantage of the sample holder of the invention is that, while providing good analytical results, it can be sufficiently inexpensive to be discarded after use. Thus, the need to clean and polish sample holders for reuse is avoided. Furthermore, the analyst is spared further exposure to hazardous samples as well as exposure to potentially harmful solvents such as are used in cleaning and reconditioning conventional sample holders (e.g., chloroform, methylene chloride, and toluene).

Also, if desired, the sample holder can be stored or archived for future reference. For instance, comparing the spectra of materials with the spectra of known standard samples and, in some instances, comparing spectra during the course of a chemical reaction or process can be necessary or desirable. The sample holder of the present invention can be stored with samples applied thereto, and analyzed at a later date with little or no degradation in the spectra of many samples. Due to the microporous structure of the sheet, the sample typically penetrates the pores in the sheet and is securely held on the sheet. Thus, there is typically little tendency to lose sample from the surface. Additionally, due to the chemical inertness of, for example, microporous polyethylene, there is little tendency of the sample to react with the sheet and thereby be altered or degraded.

Accordingly, sample holders of the invention are well-suited for use in aging and degradation studies of materials.

The baseline transmittance of the sample holder can be determined prior to applying the sample thereto. If desired and if the sample is a material that is soluble, it may be dissolved in a suitable solvent (e.g., water, toluene, methylene chloride, methyl ethyl ketone, etc.) prior to applying the sample to the sample holder. Solvents may be used to facilitate handling of sample materials and/or obtaining sample materials, e.g., by extraction. Samples in the form of fine particles and powders can be directly analyzed (i.e., quantified) on sample holders of the invention without being solubilized if desired.

In a simple embodiment, a supply (e.g., roll of microporous sheet material) with a sample thereon can be fed into a spectroscopic analyzing device, secured in position and held flat by support members such as clips or brackets on the device. In this embodiment of the invention, the support member engages releasably with the sheet.

Objects and advantages of this invention are further illustrated by the following examples. The particular materials and amounts thereof, as well as other conditions and details, recited in these examples should not be used to unduly limit this invention.

EXAMPLES

Example 1

A sample holder was prepared by securing a nonwoven microporous polyethylene membrane with a thickness of about 0.125 mm and approximately 88% void volume (prepared according to U.S. Pat. No. 4,539,256, the teaching of which is incorporated herein by reference) between two sheets of paperboard stock measuring approximately 5 cm×10 cm having openings cut therein of approximately 19 mm diameter, such that the openings in the two paperboard sheets were exactly aligned and the web extended across the openings. The paperboard stock was RF-sealed at its periphery, which fixed the polyethylene web in place. A sample retaining means, centered in the opening, was formed by placing the sample holder on a flat steel plate and embossing a 12 mm i.d.×14 mm o.d. ring in the exposed portion of the web by striking a circular steel die against the web. The sample platform was found to have a volume of 11.8 µL.

Example 2

Sample holders of the invention were prepared as described in Example 1 (except that an arbor press was used to form the sample confining means) for comparison to a known quantitative FT-IR method using a KBr cell.

Twenty-nine samples of diesel engine oil, both new and used, were analyzed in a Model SL-3 KBr cell having a 100 µm path length (International Crystal Laboratories; Garfield, N.J.) for soot, oxidation products, nitrogen oxides, sulfation products, diesel fuel content, and glycol content, in accordance with methods described in "Used Lubricating Oil Analysis," Nicolet Instrument Corporation (1995), using a Nicolet 710 FT-IR spectrometer. In the method, IR absorption at various wavenumbers for used oil is compared against absorption recorded for new oil, and the differences in absorption are correlated to breakdown of engine oil or of changes to additives in the oil. Components are shown in Table 1.

TABLE 1

| Component | Approximate Location |
| --- | --- |
| soot | baseline near 2000 $cm^{-1}$ compared with background |
| oxidation products | peak near 1700 $cm^{-1}$ |
| nitrogen products | peak near 1630 $cm^{-1}$ |
| sulfation products | peak at 1150 $cm^{-1}$ |
| diesel fuel | peak near 800 $cm^{-1}$ |
| glycol | peaks near 880, 1040, and 1080 $cm^{-1}$ |

Absorption values for the 29 samples were then obtained using a sample holder of the invention. A 12 µL aliquot of an engine oil sample to be analyzed was measured onto a brass button (with a smooth upper surface) of approximately 12 mm in diameter. A microporous sample platform (e.g., item 28 from FIG. 2) was placed directly on the oil sample and held in place until the oil sample had completely penetrated the sample platform area (approximately 30 seconds, depending on oil viscosity).

The sample holder then was placed in a conventional apparatus in the same FT-IR spectrophotometer as was used in the cell analysis, and IR spectra of the oil samples were taken. Absorption at the indicated wavenumbers was recorded and compared to values obtained using the cell. All data was collected and analyzed using the OMNIC™ Integra software (Nicolet Instrument, Corp.) resident on the spectrophotometer.

FIGS. 7–12 show the correlation of values obtained by the two methods. In each plot, quantitative data obtained by use of a conventional IR cell is plotted against the same data element obtained from the same sample by use of the inventive sample holder. Straight line relationships indicate satisfactory correlation of data obtained by the two methods.

Figure 7:
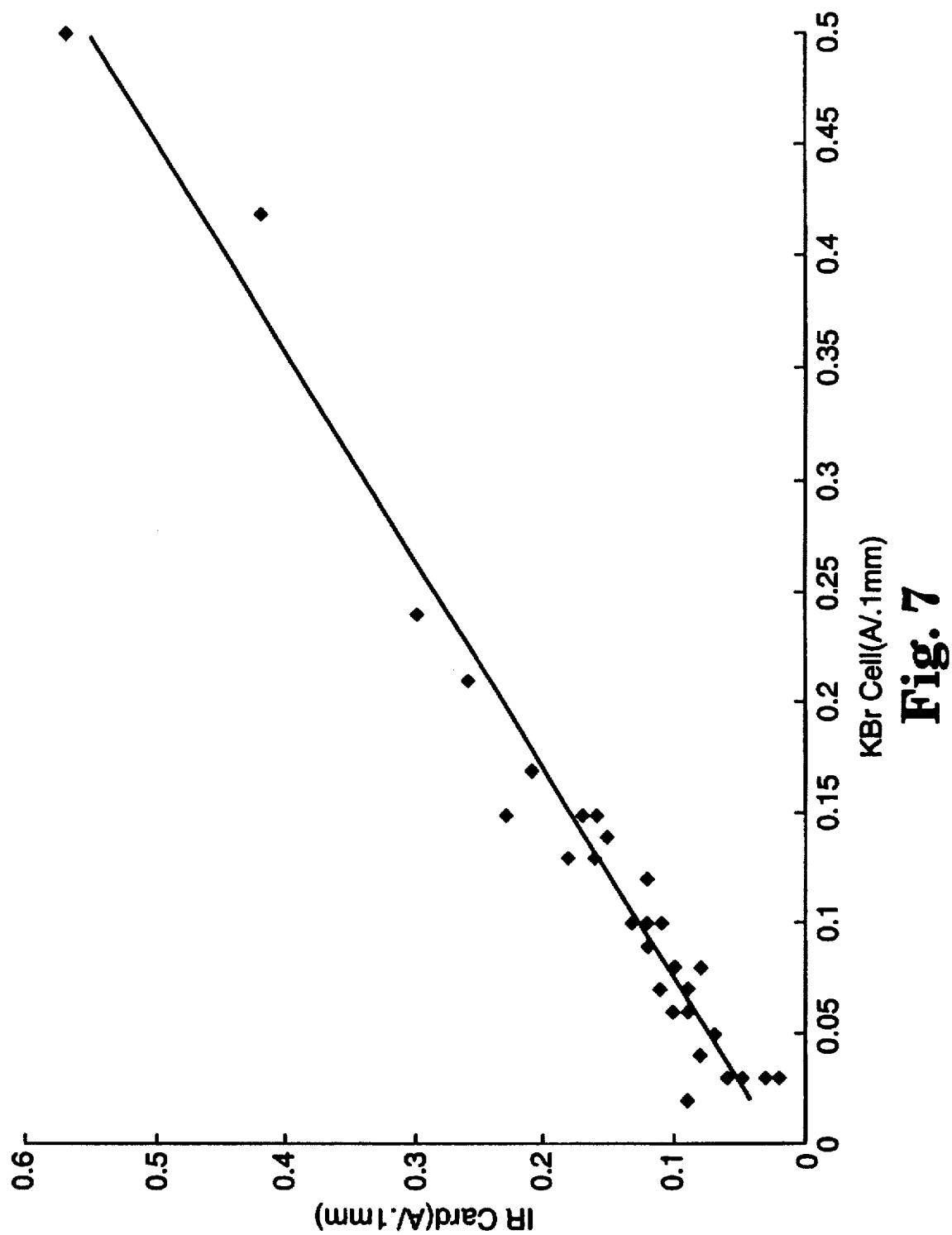
FIG. 7 is a comparative plot of IR absorbance measurement of engine oil oxidation using a sample holder of the present invention against IR absorbance measurement of engine oil oxidation using a KBr cell.
Figure 8:
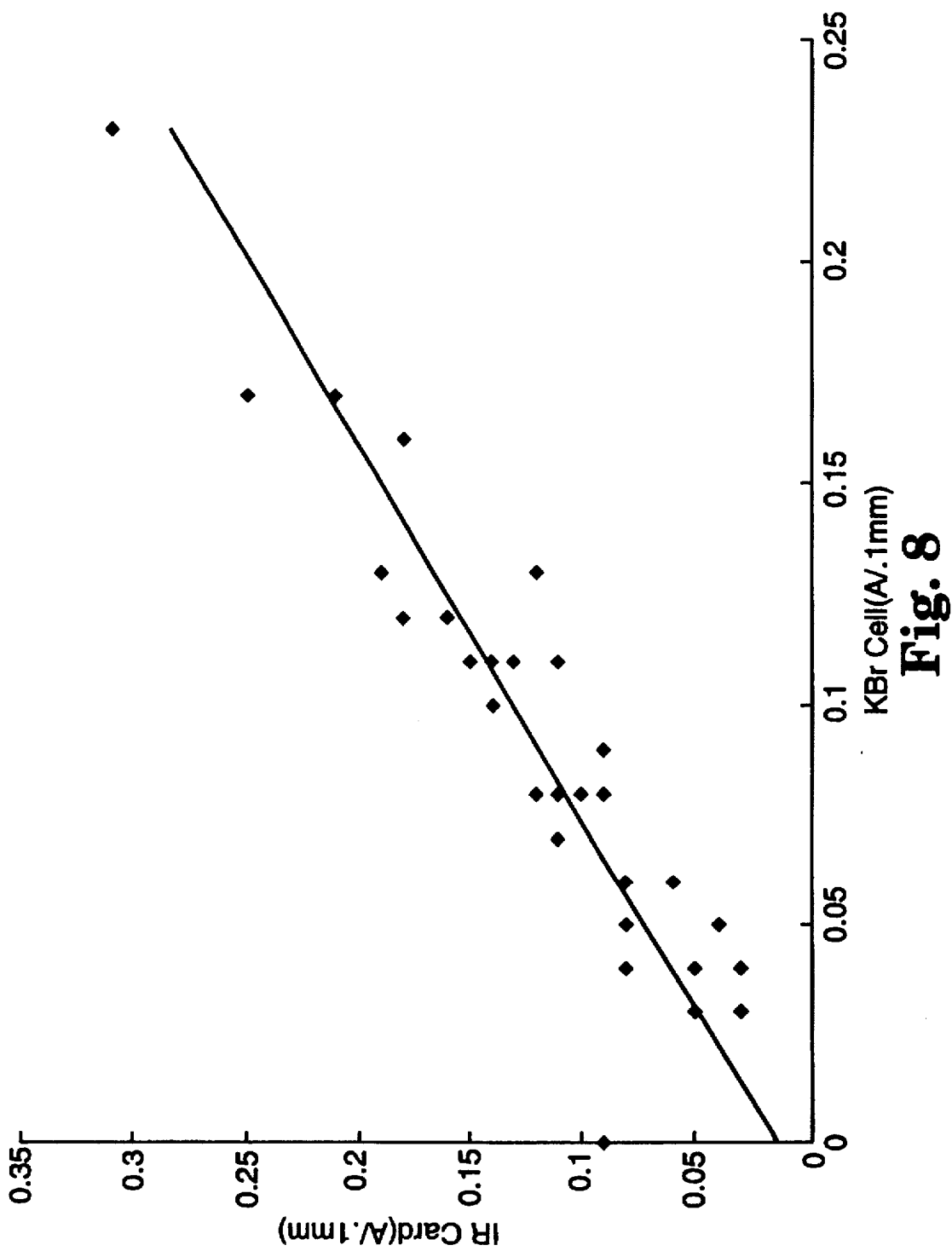
FIG. 8 is a comparative plot of IR absorbance measurement of engine oil nitration using a sample holder of the present invention against IR absorbance measurement of engine oil nitration using a KBr cell.
Figure 9:
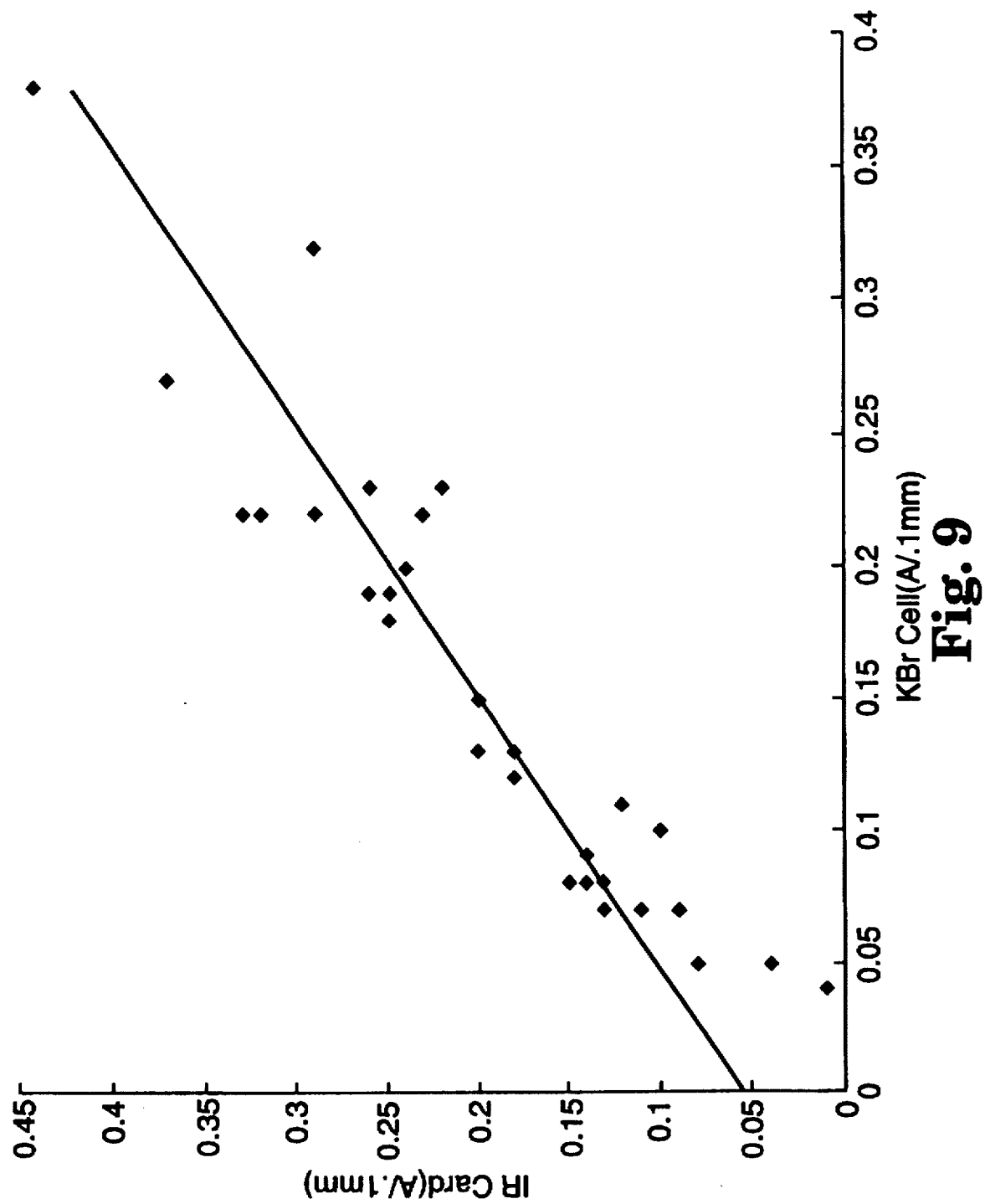
FIG. 9 is a comparative plot of IR absorbance measurement of engine oil sulfation using a sample holder of the present invention against IR absorbance measurement of engine oil sulfation using a KBr cell.

FIGS. 7, 8, and 9 show correlations of quantitative measurements taken of engine oil oxidation, nitration, and sulfation, respectively. For the sake of convenience, the OMNIC™ Integra 1.0a software resident on the spectrophotometer normalized the path length for both the conventional IR cell and the sample holder of the invention to be 0.1 mm.

Figure 10:
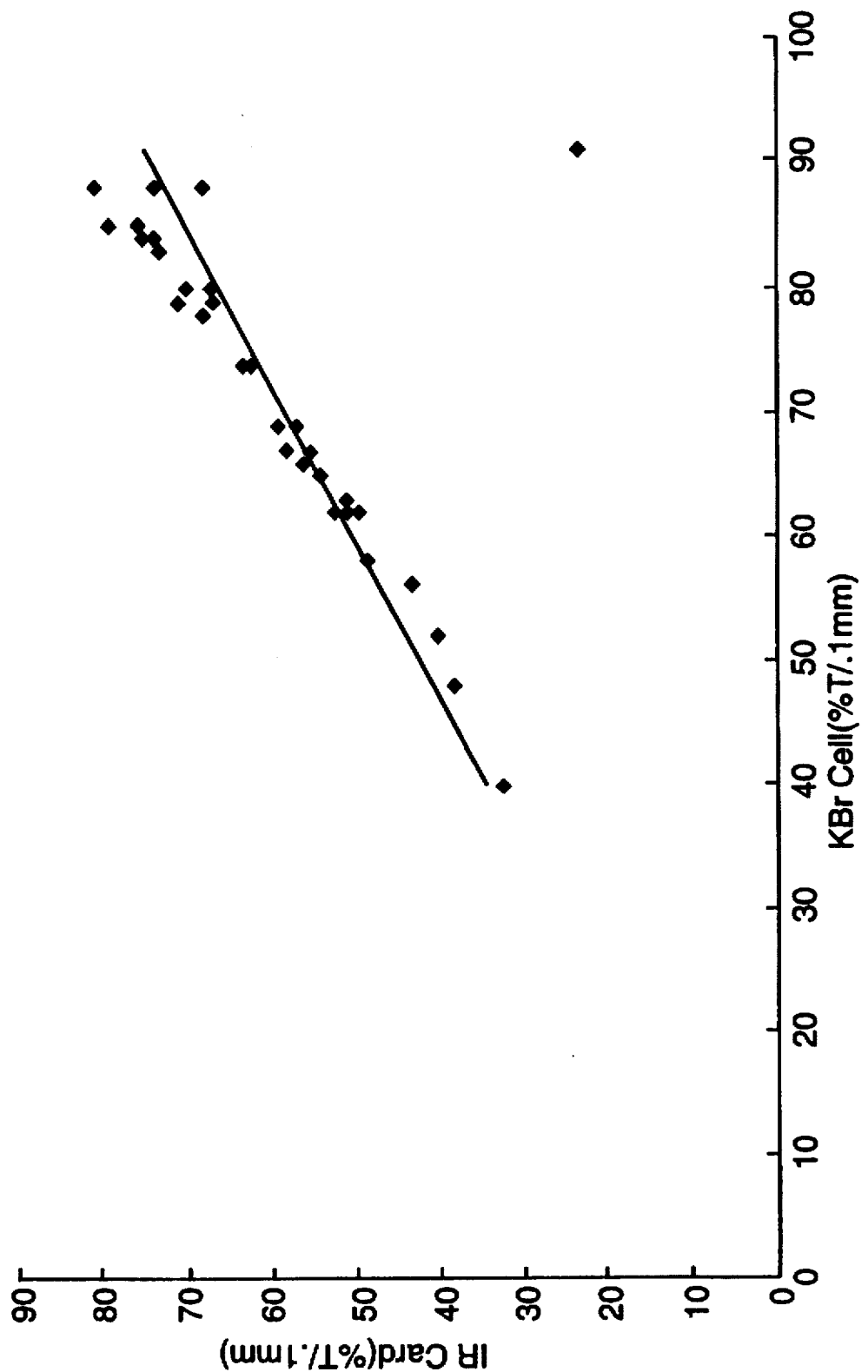
FIG. 10 is a comparative plot of IR transmittance measurement of engine oil soot content using a sample holder of the present invention against IR transmittance measurement of engine oil soot using a KBr cell.

FIG. 10 shows the correlation of soot measured by each method for each sample. Quantification was reported as transmittance per 0.1 mm to emphasize the fact that soot rendered the oil more opaque. Again, path lengths for both methods were normalized to 0.1 mm by spectrophotometer software.

Figure 11:
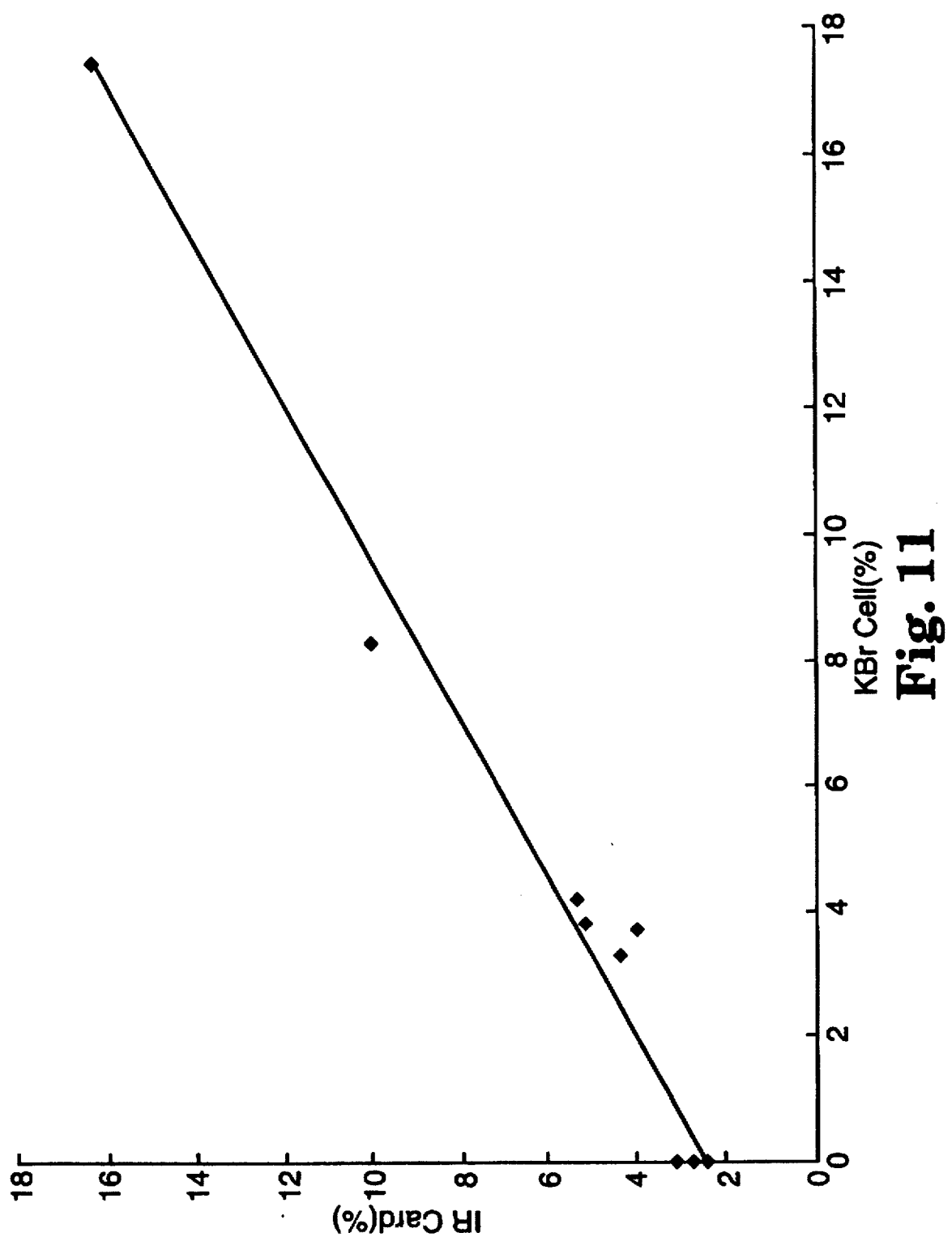
FIG. 11 is a comparative plot of diesel fuel concentration in engine oil as obtained by IR absorbance measurement using a sample holder of the present invention against diesel fuel concentration in engine oil as obtained by IR absorbance measurement using a KBr cell.
Figure 12:
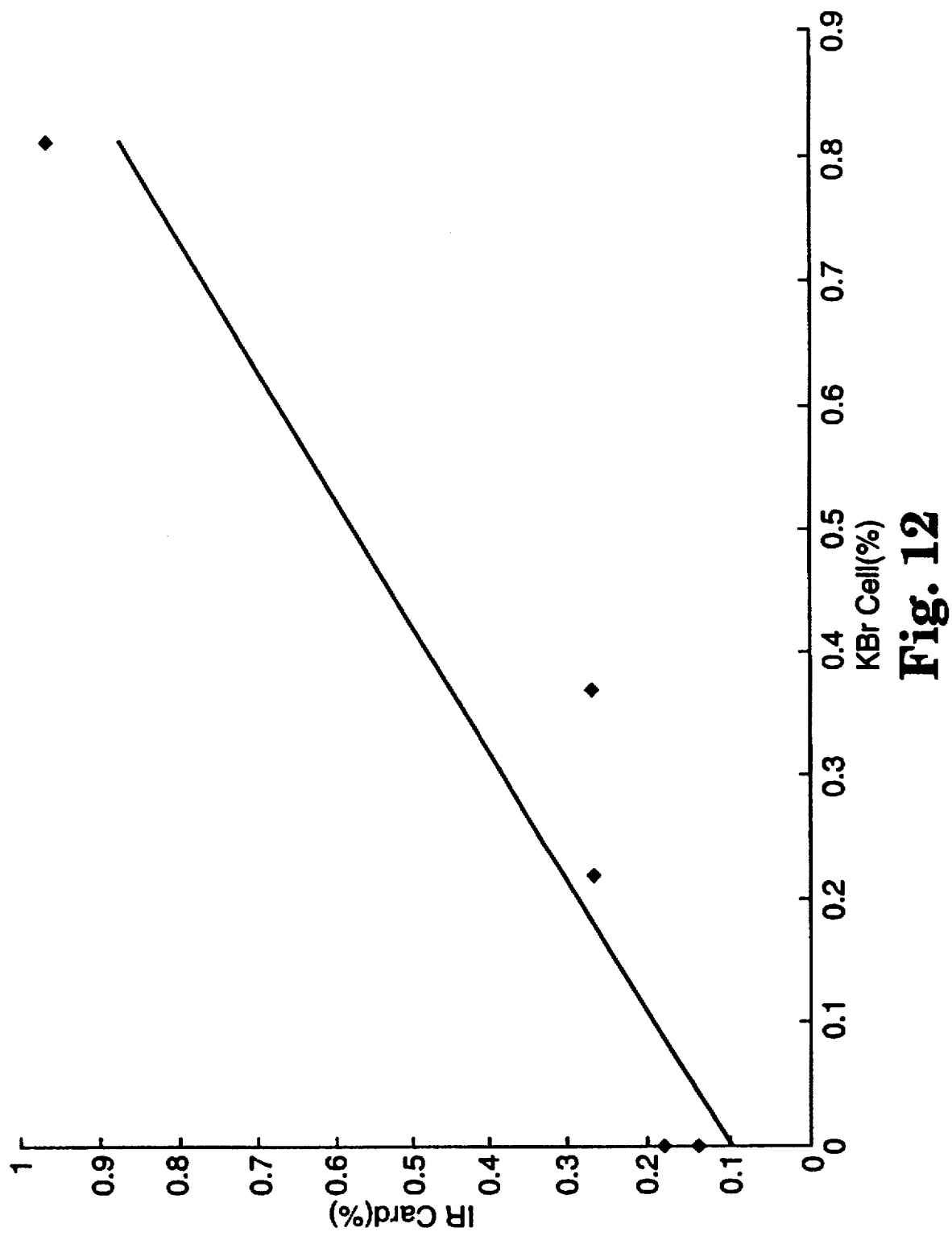
FIG. 12 is a comparative plot of glycol concentration in engine oil as obtained by IR absorbance measurement using a sample holder of the present invention against glycol concentration in engine oil as obtained by IR absorbance measurement using a KBr cell.

In FIGS. 11 and 12, diesel fuel and glycol in the engine oil were measured respectively and reported as percent concentration in each sample, as calculated by the OMNIC™ Integra 1.0a software.

All trend lines were obtained using Microsoft™ Excel™ 5.0 software.

Various modifications and alterations of this invention that do not depart from the scope and spirit of this invention will become apparent to those skilled in the art.

What is claimed is:

1. A device for holding a sample to be spectroscopically analyzed, said device comprising:

a porous medium for receiving said sample, said porous medium comprising a nonporous region for confining said sample within a predetermined portion of said porous medium, said nonporous region defining said predetermined portion.

2. The device of claim 1 wherein said porous medium is a screen comprising a plurality of unobstructed openings, the cross-sectional area of each of said openings being such that said sample is retained on said screen by the surface tension of said sample.

3. The device of claim 1 wherein said porous medium is a microporous sheet.

4. The device of claim 3 wherein said microporous sheet has a void volume of at least 20%.

5. The device of claim 3 wherein said microporous sheet comprises a polymer.

6. The device of claim 5 wherein said polymer is polyethylene, polypropylene, copoly(ethylene-propylene), polytetrafluoroethylene, poly(vinyl chloride), polycarbonate, poly(vinylidene fluoride), cellulose acetate, cellulose nitrate, poly(chlorotrifluoroethylene), polyester, or nylon.

7. The device of claim 3 wherein said nonporous region is an embossed compression in said microporous sheet.

8. The device of claim 1 wherein the area of said predetermined portion is between about 1 and about 6 cm$^2$.

9. The device of claim 1 wherein said porous medium comprises two or more of said predetermined portions.

10. The device of claim 1 further comprising a frame, said frame comprising an upper surface, a lower surface, and at least one aperture extending from said upper surface through said lower surface, said porous medium being held within said frame and extending across said aperture.

11. The device of claim 10 wherein said frame holds said porous medium substantially flat across said aperture.

12. The device of claim 10 wherein said porous medium is a screen comprising a plurality of unobstructed openings, the cross-sectional area of each of said openings being such that said sample is retained on said screen by the surface tension of said sample.

13. The device of claim 10 wherein said porous medium is a microporous sheet.

14. The device of claim 13 wherein said microporous sheet has a void volume of at least 20%.

15. The device of claim 13 wherein said microporous sheet comprises a polymer.

16. The device of claim 15 wherein said polymer is polyethylene, polypropylene, copoly(ethylene-propylene), polytetrafluoroethylene, poly(vinyl chloride), polycarbonate, poly(vinylidene fluoride), cellulose acetate, cellulose nitrate, poly(chlorotrifluoroethylene), polyester, or nylon.

17. The device of claim 13 wherein said nonporous region is an embossed compression in said microporous sheet.

18. The device of claim 10 wherein the area of said predetermined portion is between about 1 and about 6 cm$^2$.

19. The device of claim 10 comprising two or more apertures, each aperture having a porous medium for receiving a sample extending thereacross.

20. A method of spectroscopically analyzing a sample comprising the steps:

a) transmitting infrared radiation through a sample that has been applied to the predetermined portion of a device for holding a sample to be spectroscopically analyzed, said device comprising a porous medium for receiving said sample, and a nonporous region for confining said sample within a predetermined portion of said porous medium, said nonporous region defining said predetermined portion; and b) analyzing the radiation transmitted through said sample and said porous medium.

21. The method of claim 20 further comprising the step of determining the baseline transmittance of said device prior to applying said sample thereto.

22. The method of claim 20 wherein said sample is applied to said device by filtering a stream containing said sample through said predetermined portion of said porous medium.

23. The method of claim 20 wherein said porous medium is a microporous sheet.

24. A method of spectroscopically analyzing a sample comprising the steps:

a) transmitting infrared radiation through a sample that has been applied to the predetermined portion of a device for holding a sample to be spectroscopically analyzed, said device comprising a porous medium for receiving said sample, and a nonporous region for confining said sample within a predetermined portion of said porous medium, said nonporous region defining said predetermined portion, and a frame comprising an upper surface, a lower surface, and at least one aperture extending from said upper surface through said lower surface, said porous medium being held within said frame and extending across said aperture; and b) analyzing the radiation transmitted through said sample and said porous medium.

25. The method of claim 24 further comprising the step of determining the baseline transmittance of said device prior to applying said sample thereto.

26. The method of claim 24 wherein said sample is applied to said device by filtering a stream containing said sample through said predetermined portion of said porous medium.

27. The method of claim 24 wherein said porous medium is a microporous sheet.

* * * * *